United States Patent [19]
Sakai et al.

[11] Patent Number: 5,478,526
[45] Date of Patent: Dec. 26, 1995

[54] NOZZLE-TYPE ANALYSIS APPARATUS

[75] Inventors: Tadashi Sakai; Hitoshi Yagi, both of Yokohama, Japan

[73] Assignee: Kabushiki Kaisha Toshiba, Kawasaki, Japan

[21] Appl. No.: 282,469

[22] Filed: Jul. 29, 1994

Related U.S. Application Data

[63] Continuation of Ser. No. 40,858, Mar. 31, 1993, abandoned.

[30] Foreign Application Priority Data

Mar. 31, 1992 [JP] Japan ..................................... 4-077336

[51] Int. Cl.$^6$ ................................................. G01N 33/00
[52] U.S. Cl. ................... 422/81; 422/68.1; 422/82.01; 422/82.02; 422/82.03; 422/100; 422/103; 204/416; 204/418; 204/419; 257/213
[58] Field of Search ..................... 422/63, 68.1, 81, 422/82.01, 82.02, 82.03, 100, 102, 103; 204/416, 418, 419, 153.15; 257/213

[56] References Cited

U.S. PATENT DOCUMENTS

| | | | |
|---|---|---|---|
| 4,020,830 | 5/1977 | Johnson et al. | 204/418 X |
| 4,269,682 | 5/1981 | Yano et al. | 204/418 |
| 4,318,884 | 3/1982 | Suzuki | 422/63 |
| 4,318,885 | 3/1982 | Suzuki et al. | 422/100 X |
| 4,502,938 | 3/1985 | Covington et al. | 204/418 X |
| 4,505,799 | 3/1985 | Baxter | 204/416 |
| 4,636,827 | 1/1987 | Rudolf | 204/416 X |
| 4,680,270 | 7/1987 | Mitsumaki et al. | 422/81 X |
| 4,758,325 | 7/1988 | Kanno et al. | 204/411 |
| 4,791,465 | 12/1988 | Sakai et al. | 357/25 |
| 4,838,999 | 6/1989 | Haar et al. | 422/82.03 X |
| 4,897,244 | 1/1990 | Wallace et al. | 422/100 |
| 4,961,833 | 10/1990 | Sakai et al. | 204/416 X |
| 5,011,589 | 4/1991 | Amemiya et al. | 204/416 |
| 5,138,251 | 8/1992 | Koshiishi et al. | 204/416 X |

FOREIGN PATENT DOCUMENTS 56-81451  7/1981  Japan.

OTHER PUBLICATIONS

Merck Index—10th edition, p. 7458, 1983.

*Primary Examiner*—James C. Housel
*Assistant Examiner*—Maureen M. Wallenhorst
*Attorney, Agent, or Firm*—Oblon, Spivak, McClelland, Maier & Neustadt

[57] ABSTRACT

A nozzle-type analysis apparatus for sucking a sample solution in a sample vessel for analyzing the sample solution. A sample suction nozzle for sucking the sample solution stored in the sample vessel and a solution component sensor having a sensor forming portion formed integrally with a front end portion of the sample suction nozzle to be inserted into the sample vessel are provided. The integral structure of the sample suction nozzle and the solution component sensor has a size capable of being inserted into the sample vessel, the solution component sensor having a sensor output portion effected with a water-resistant insulation layer. A hydrophobic film is further formed on the surface of the sensor a coat treatment. A sample flow shut-out valve is disposed in the sample flow passage at a portion between the front end of the sample suction nozzle and the sensor forming portion of the solution component sensor.

31 Claims, 11 Drawing Sheets

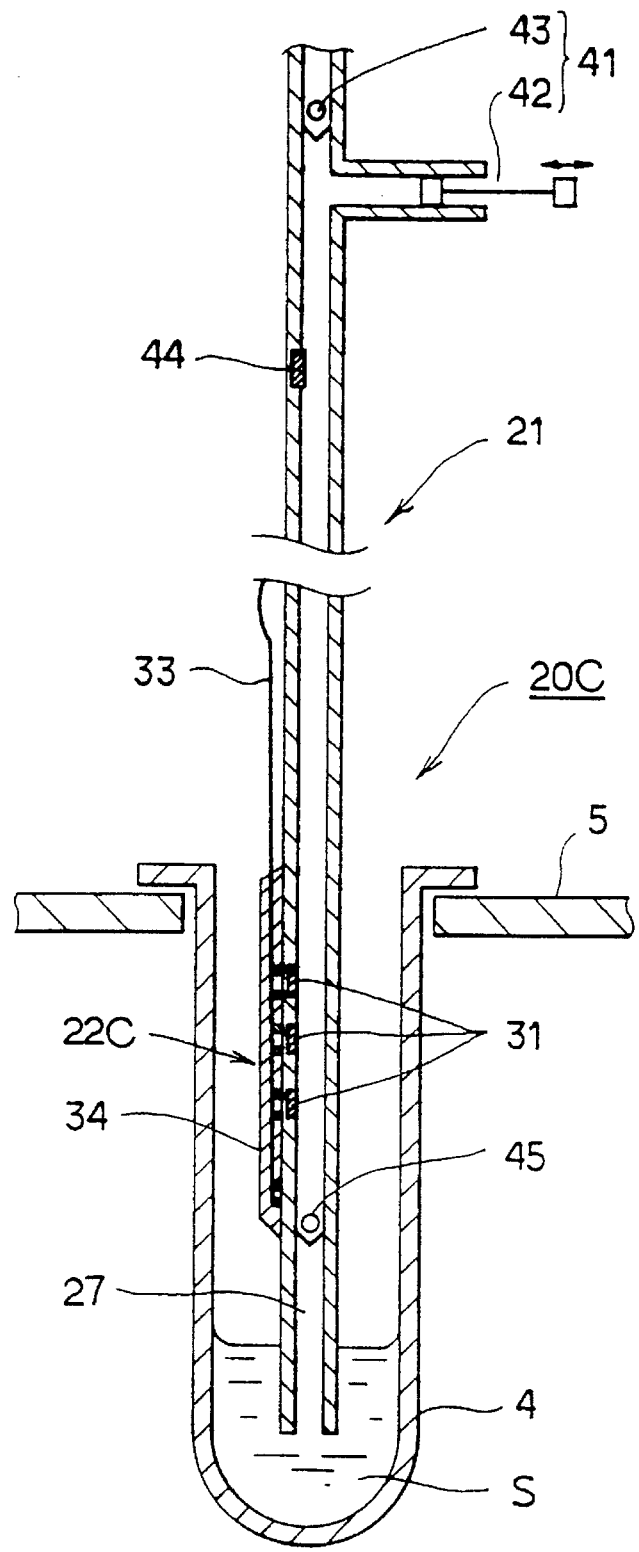
F I G. 7

NOZZLE-TYPE ANALYSIS APPARATUS

This application is a continuation of application Ser. No. 08/040,858, filed on Mar. 31, 1993, now abandoned.

BACKGROUND OF THE INVENTION

The present invention relates to an automatic chemical or biochemical analysis apparatus for automatically measuring a quantity of a specific chemical or biochemical substance contained in a material to be analized and, more particularly, to a nozzle-type analysis apparatus adapted to measure a trace quantity of material to be analized such as blood specimen.

Recently, in a biochemical automatic analysis apparatus for automatically measuring a quantity of a specific chemical substance contained in a material to be analized such as blood specimen, it has been required to inspect many kinds of inspection items, to reduce a quantity of a material required, to improve an inspection speed and the like.

In order to satisfy these requirement, one measure is to minimize an order of quantity of the material to be measured for one inspection item such as to 1 micron (1μ) order. One conventional biochemical automatic analysis apparatus has such a structure as shown in Figs. 10 and 11. Referring to FIGS. 10 and 11, A blood serum S as a sample to be analyzed is stored in a primary vessel 2 supported by a sample disc 1, and a plurality of primary sample vessels 2 are generally supported by the disc 1.

An automatic analysis of the blood serum sample S contained in the primary sample vessel 2 is perfomed by first sampling the blood serum sample S from the primary sample vessel 2 by means of a sampling nozzle 3 and then delivering the sample S into a sample vessel 4. A plurality of sample vessels 4 are disposed to a reaction disc 5 and necessary reagent or reagents are then delivered into the respective sample vessels 4 through a reagent delivering nozzle 8 from reagent vessels 7 supported by a reagent disc 6.

After the addition of the reagent into the sample vessels 4, an analyzer light is irradiated to the respective sample vessels 4 through an optical measurement system 9 to thereby carry out an absorption analysis, and on the while, as shown in FIG. 11, the blood serum sample S in the sample vessel 4 is sucked by a sample suction nozzle 10 for an electrolyte measurement and then supplied to a flow-through type ion sensor system 11 for the electrolyte measurement as a nozzle-type analysis apparatus, thus performing an electrolyte analizing operation.

FIG. 11 represents the flow-through type ion sensor system 11 as one example of a conventional electrolyte measurement system performing the electrolyte analysis. Referring to FIG. 11, the blood serum sample S is sucked, by immersing the front end of the sample suction nozzle 10 communicated with a flow cell 12 into the sample vessel 4 supported by the reaction disc 5, into the flow cell 12 of the ion sensor system 11 from the sample vessel 4. The flow cell 12 is accommodated in a constant temperature jacket 13 for keeping constant temperature of each sensor disposed in the flow cell 12 and the blood serum sample S by circulating hot water of constant temperature in the constant temperature jacket 13 through a constant temperature water circulation system 14. A signal from each sensor disposed in the flow cell 12 is transmitted externally to thereby carry out the electrolyte analysis.

In FIG. 10, the automatic analysis system includes a washing unit 16 for the sample vessels, a sampling nozzle arm 17, a reagent nozzle arm 18, a black box 19a of the optical measurement system 9 and a light source 19b.

In the conventional flow-through type ion sensor system 11 of the structure described above, the sample suction nozzle 10 is directly immersed or dipped into the blood serum sample S in the sample vessel 4 to suck the sample and supply it into the flow cell 12 by means of the sample suction nozzle 10. According to this ion sensor system 11, the sample suction nozzle 10 has a nozzle portion having a relatively long length extending between the sample vessel 4 and the flow cell 12. This involves a problem of requiring an extra quantity of blood serum sample solution corresponding to an inner volume of this nozzle portion. Furthermore, an extremely large quantity of blood serum sample is required for the electrolyte measurement in comparison with other inspection or analysis items, so that reduction of the quantity of the sample to be used for the electrolyte measurement has been desired for achieving necessary trace quantity analysis.

Still furthermore, although the temperature of the sample vessel 4 is maintained to the constant temperature of 37° by a constant temperature tank, not shown, disposed below the reaction disc 5, it is difficult to maintain a temperature in an upper space, in which the suction nozzle arm and others are elevated, to the constant temperature. In order to obviate this defect, it is necessary to locally dispose the constant temperature jacket 13 to the flow cell positioned at the upper end of the material suction nozzle 10, resulting in the location of a specific temperature control system or hot water-circulation system 14, making complicated the electrolyte measurement system itself and making difficult to exchange a sensor cell.

Although the trace quantity analysis of the sample to be analized may be performed by making small an inner diameter of a sample flow passage, the reduction of the inner diameter will results in a lowering of a conductance of the sample flow passage, which hence results in a time lag between the sucking operation of a sample suction pump, not shown, disposed with a space along the sample flow passage and an actual sample sucking operation, thus being inconvenient.

Moreover, according to this time lag, so-called a trailing phenomenon of the sample solution is caused after the stopping of the operation of the suction pump and the stabilization of an output is hence delayed, resulting in the slow-down of a treating speed. In order to avoid this problem of the trailing phenomenon, the sample suction nozzle 10 may be maintained in a state immersed in the sample solution S, but in this state, the flow cell sensor likely picks up noises from a solution surface of the sample solution S. This will results in degradation of the measurement performance.

SUMMARY OF THE INVENTION

An object of the present invention is to substantially eliminate defects or drawbacks encountered in the prior art and to provide a nozzle-type analysis apparatus capable of reducing a quantity of sample solution necessary for the electrolyte measurement analysis and making compact the electrolyte measurement system by eliminating the constant temperature providing means.

Another object of the present invention is to provide a nozzle-type analysis apparatus capable of reducing a quantity of liquid material necessary for the flow analysis of the electrolyte and realizing analysis and measurement of the material to be analyzed with high performance by surely preventing the material liquid from trailing at the material suction time.

These and other objects can be achieved according to the present invention by providing a nozzle-type analysis apparatus for sucking a sample solution in a sample vessel for analyzing the sample solution comprising:

- a sample suction nozzle means for sucking the sample solution stored in the sample vessel; and
- a solution component sensor means having a sensor forming portion formed integrally with a front end portion of the sample suction nozzle means to be inserted into the sample vessel, the integral structure of the sample suction nozzle means and the solution component sensor means having a size capable of being inserted into the sample vessel, the solution component sensor means having a sensor output portion effected with a water-resistant insulation layer.

In preferred embodiments, the solution component sensor comprises a flow cell sensor which comprises a flow cell body, a plate-shaped sensor chip bonded to the flow cell body and a sample flow passage formed in an axial direction of the flow cell body.

A nozzle chip and a sample suction tube are preliminarily integrally formed to flow cell body.

The nozzle-type analysis apparatus further comprises a sample flow shut-out valve means disposed in the sample flow passage at a portion between the front end of the sample suction nozzle and the sensor forming portion of the solution component sensor means.

The sample flow shut-out valve means comprises a check valve.

The sample flow shut-out valve means is integrally formed to the flow cell sensor and is a microvalve composed of a piezoelectric element, a valve sheet and a valve diaphragm displaceable towards the valve sheet. The solution component sensor comprises a flow cell sensor which comprises a flow cell body, a sensor chip bonded to said flow cell body and a sample flow passage formed in an axial direction of the flow cell body, and the microvalve is disposed at a flow change portion in the sample flow passage. The flow cell sensor comprises a flow cell body as a base silicon substrate, a sensor plate forming a sensor chip formed on one side of the flow cell sensor and a cover member disposed on another side of the flow cell sensor, the sample flow passage being formed between the sensor chip and the cover member.

The sample flow passage is composed of a V-shaped groove in section formed by effecting an isotopic etching treatment to a silicon substrate.

The flow cell body has a surface coated with a hydrophobic film to eliminate surface contamination. The sensor chip is composed of a silicon substrate having a multi-layer structure. The silicon substrate has one surface to which a plurality of field effect transistors are formed in a row, and the silicon substrate has another surface to which a plurality of openings are formed at portions corresponding to the location of the field effect transistors and gate insulation films or gate passivation films are formed on surfaces of the field effect transistors on the sides exposed to the openings to thereby form sensor sensitive portions.

A hydrophobic film is further formed on the surface of the flow cell sensor by coating an ethylene fluoride on the surface.

According to the nozzle-type analysis apparatus of the characters described above, a dead space of inner volume of the nozzle portion of the apparatus for sucking a solution to be analyzed from the sample vessel can be remakably reduced, thus effectively reducing the quantity of the sample solution to be used for the analysis. The shortening of the nozzle portion can reduce the time when the sample solution has been introduced into the sensor portion, so that the potential response can be made fast and the sample treating efficiency can be hence improved.

Furthermore, the sample solution can be measured under the sensor portion being retained in the sample vessel, so that any constant temperature keeping means cannot be located for the flow cell and the sample can be analyzed with the temperatures of the sample and the sensor being maintained constant in the sample vessel, thus making compact the structure of the apparatus.

In a preferred embodiment, since the flow shut-out valve is disposed in the sample flow passage at a portion between the nozzle front end and the sensor forming portion of the flow cell sensor, the trailing phenomenon of the sample solution after the sucking operation can be substantially eliminated, thus shortening the time to the establishment of the stable output after the sucking operation. Furthermore, the conductive resistance can be increased by closing the shut-out valve even under the condition of the front end of the sample suction nozzle being dipped in the sample solution in the sample vessel, so that the noise level can be lowered and other troubles such as liquid dropping or air bubble involving can be also prevented by closing the shut-out valve.

BRIEF DESCRIPTION OF THE DRAWINGS

For a better understanding of the present invention and to show how the same is carried out, reference will be made hereunder, by way of a preferred embodiment, to the accomapnying drawings, in which:

FIG. 7 is an elevational section of a fourth embodiment of the nozzle-type analysis apparatus of the present invention;

DESCRIPTION OF THE PREFERRED EMBODIMENTS

One preferred embodiment of the nozzle-type analysis apparatus according to the present invention will be described hereunder with reference to the accompanying drawings.

Figure 1:
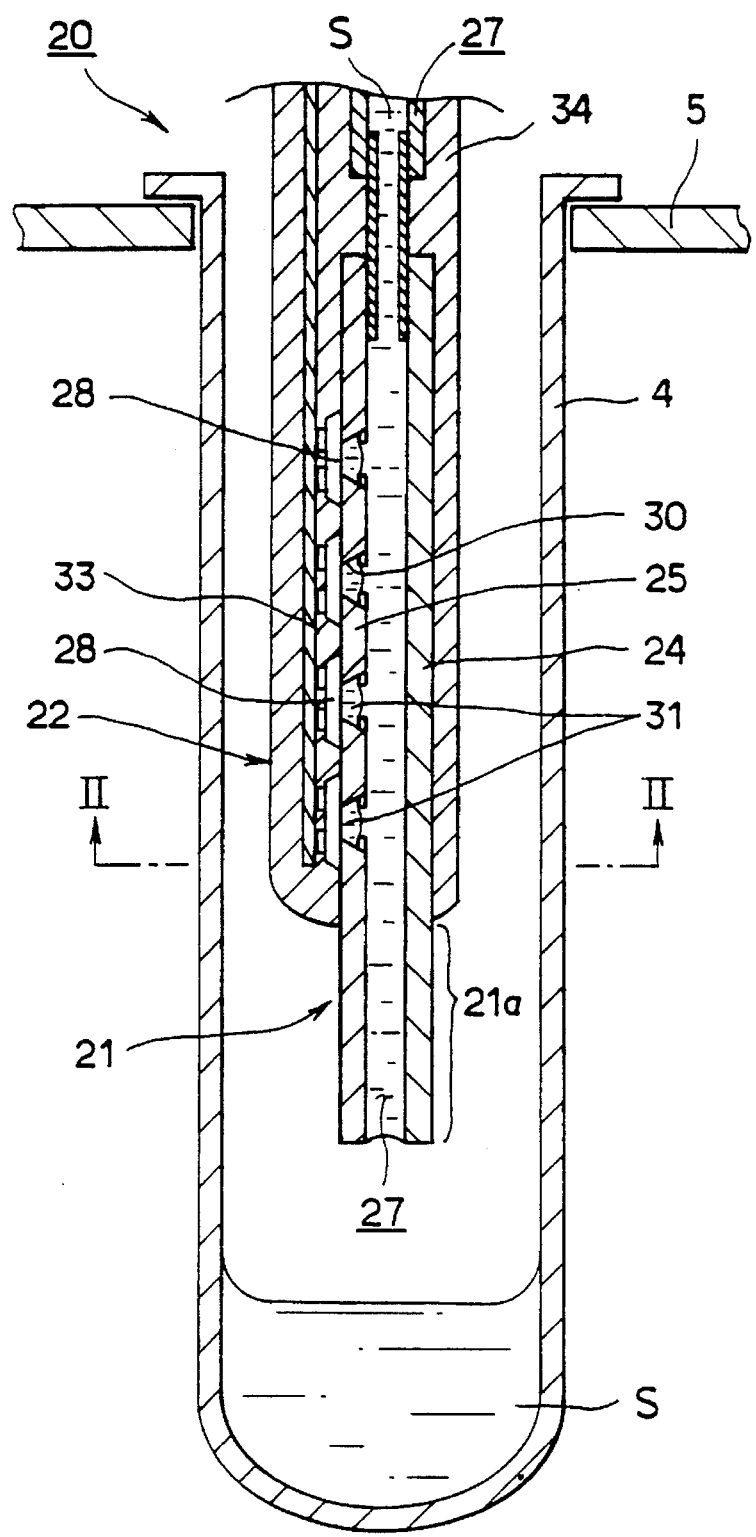
FIG. 1 is an elevational section representing a first embodiment of a nozzle-type analysis apparatus having a solution component sensor according to the present invention.
Figure 10:
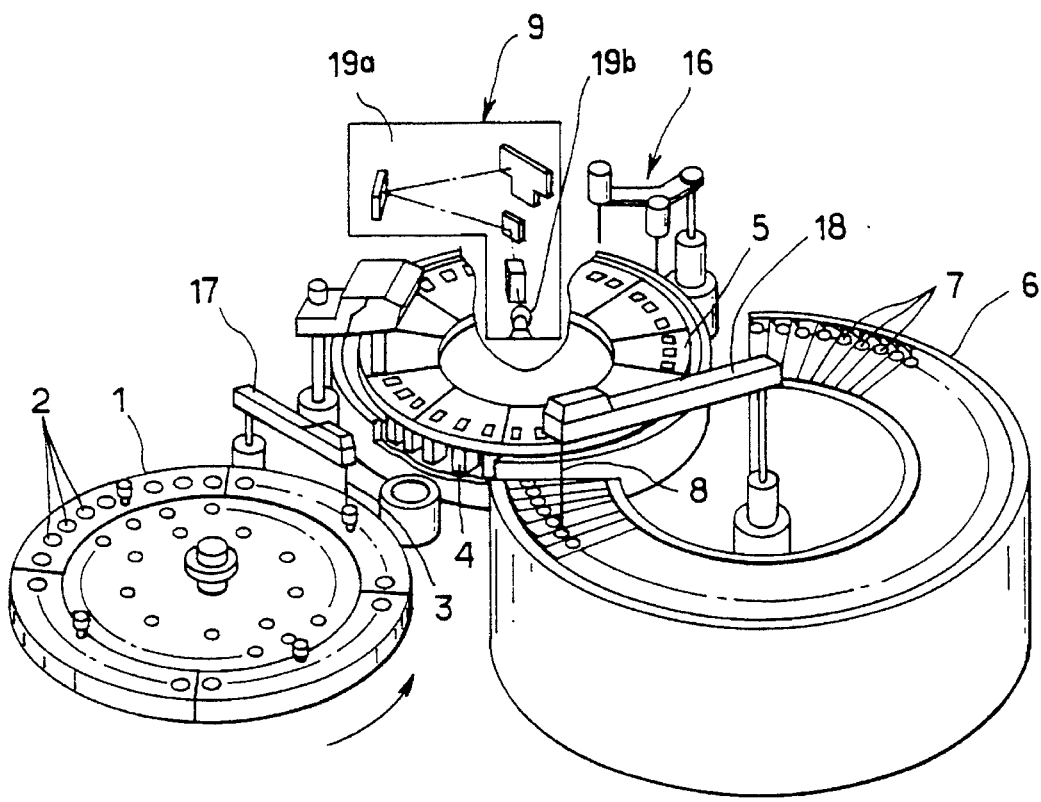
FIG. 10 is a schematic perspective view of a conventional automatic biochemical analysis system.
Figure 11:
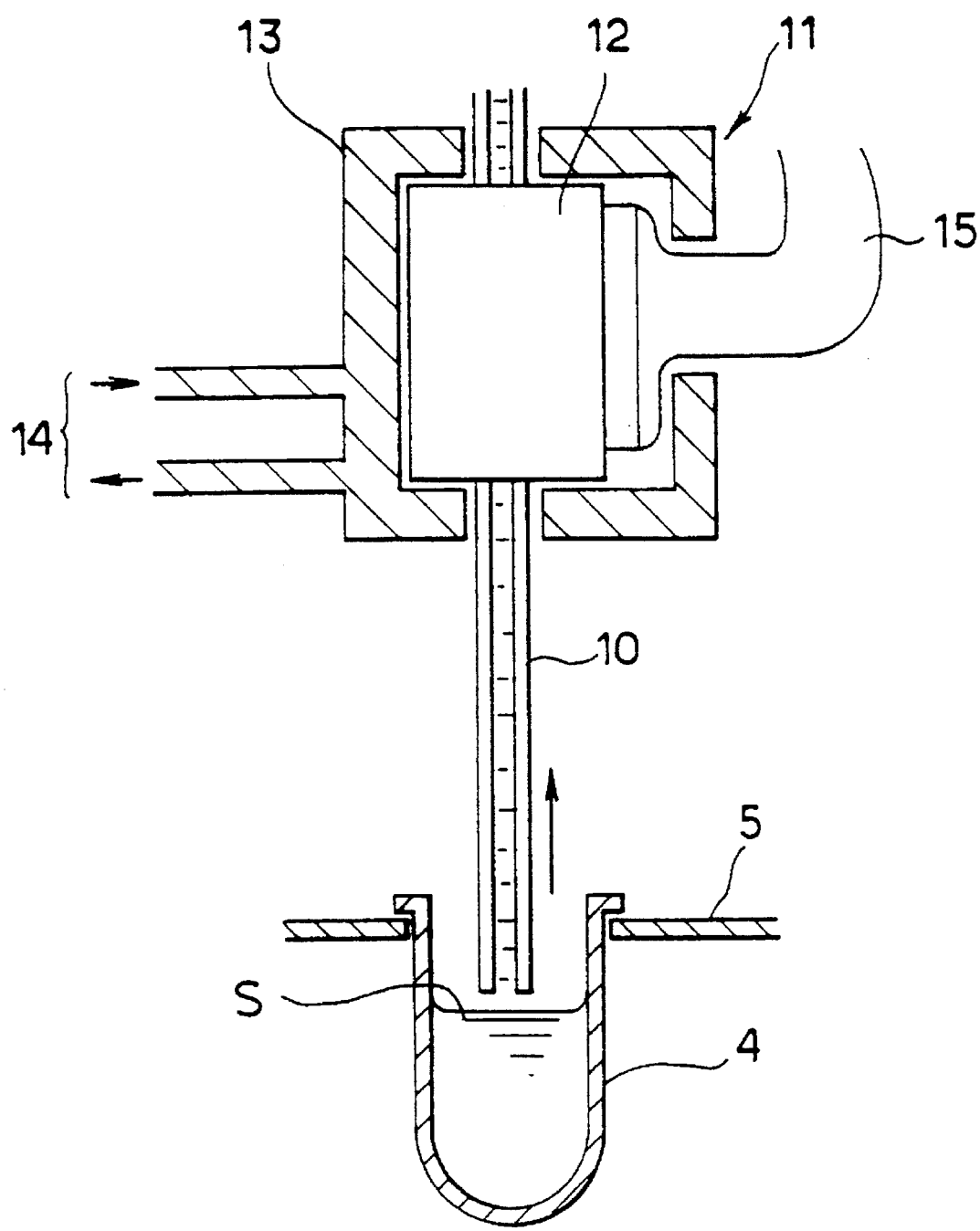
FIG. 11 is a schematic view of a flow cell type conventional measurement sensor provided for the conventional automatic biochemical analysis system such as shown in FIG. 10.

The nozzle-type analysis apparatus of the present invention is utilized for a biochemical automatic analysis system for measuring a quantity of a specific chemical substance contained in a material to be analyzed for such as blood inspection purpose. The nozzle-type analysis apparatus 20 has such a structure as shown in FIG. 1 and is utilized for an electrolyte measurement analysis system of the biochemical automatic analysis system having a structure substantially the same as that shown in FIG. 10, and accordingly, the entire structure is not shown in FIG. 1 and, like reference numerals, are added to members or elements corresponding to those shown in FIG. 10.

The nozzle-type analysis apparatus 20 has a sample suction nozzle 21, which enters or is drawn out from the sample vessel 4 supported by the reaction disc 5 as a sample vessel holder. A nozzle-type flow cell sensor 22 constituting a solution component sensor is formed integrally with or integrated with a front portion of the sample suction nozzle 21. The flow cell sensor 22 has a structure capable of being accommodated in the sample vessel 4 and also has a cross sectional area smaller than an opening cross section of the sample vessel 4. The integral structure of the flow cell sensor 22 with the sample suction nozzle 21 maintains the temperature of the flow cell sensor 22 to a constant temperature by means of a constant temperature providing tank for the sample vessel 4, thus eliminating location of an independent constant temperature jacket.

Figure 2:
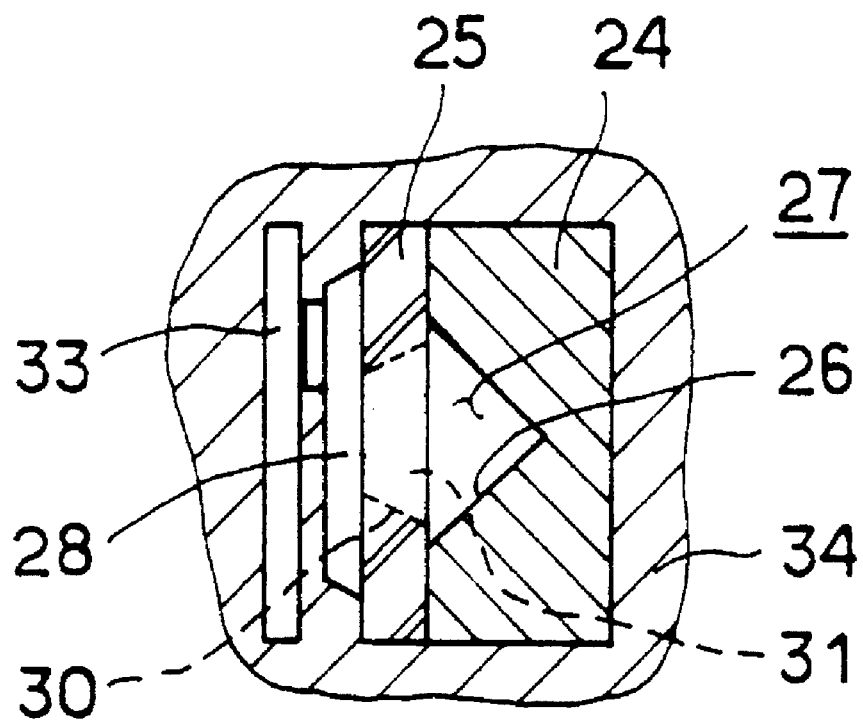
FIG. 2 is a cross section taken along the line II—II of FIG. 1.

The flow cell sensor 22 is composed of a flow cell body 24 and a plate-like sensor chip 25 formed integrally with the flow cell body 24 by electrostatic bonding means or organic bonding agent, and a sample flow passage 27 is formed in a V-shaped groove 26 as flow passage formed in the longitudinal, i.e. axial, direction of the flow cell body 24 as shown in FIG. 2. The V-shaped groove 26 can be formed by effecting an isotropic etching treatment to a silicon substrate, and the V-shaped groove 26 may be substituted with a flow passage groove having rectangular, trapezoidal or circular shape. Further, the flow cell body 24 may be formed of a glass or acrylic resin material in place of the silicon material. A hydrophobic film may be coated on the surface of the sample flow passage 27 for substantially eliminating contamination to the surface.

The sensor chip 25 is prepared by a direct bonding-type silicon substrate (wafer) having a three-layer structure of silicon/oxide-film/silicon such as that disclosed in Japanese Patent Laid-open Publication No. 62-123348 and by patterning the silicon in a stripe shape on one (first) surface of the silicon substrate to thereby form a plurality of, for example, four, field effect transistors (FET) 28, in a row, constituting a main component of the solution component sensor.

These FETs 28 are subjected to a dicing treatment by numbers corresponding to the numbers of the detection components necessary for the sensor chip 25 and then packaged. In the embodiment illustrated in FIG. 1, three elements for detecting sodium, potassium and chlorine ion components and one element for monitoring a temperature are diced in one row arrangement. The one row arrangement of the FETs 28 is effective because an outer diameter thereof is not made large even if the numbers of the required FETs 28 are increased. In an integration of four FETs 28, the sensor chip 25 has dimensions of, for example, a length of 5.6 mm, a width of 2.0 mm and a thickness of 0.2 mm.

Openings 30 are formed, by the isotropic etching treatment, on another (second) surface of the sensor chip 25 at portions corresponding to the location of the respective FETs 28. Oxide silicon gate insulation films and gate passivation films formed of such as silicon nitride are formed on the rear surfaces of the FETs 28 exposed to the bottom surface side of the openings 30 to thereby constitute sensor (gate) sensitive portions 31, respectively, as recessed portions.

To these recessed portions forming the sensor sensitive portions 31 are applied sensitive films of respectively corresponding ions. More concretely, the potassium ion film is composed of, for example, valinomycin utilized as a sensing material and polyvinyl chloride utilized as a matrix material. The sodium ion film is composed of, for example, biscrown ether utilized as a sensing material and polyvinyl chloride as a matrix material. The chlorine ion film is composed of, for example, fourth class ammonium salt utilized as a sensing material and epoxy resin utilized as a matrix material. The sensor sensitive films are formed by mixing these sensing materials and the matrix materials with a plasticizer and a solvent and potting them to the recessed portions by means of a microdispenser. In a case where cyclohexanon is utilized as the solvent, the potting treatment can be done smoothly without rapidly drying the trace quantity of original solution.

Further, although the temperature measurement can be done without specifically forming the films to the recessed portions of the FETs 28 for the temperature measurement, in such case, films only including the base matrix materials with no sensing materials may be formed. According to the formation of such films, an actual surface temperature of the sensor can be monitored with conditions approximately identical to those in the case of other sensors formed with the ion sensing films.

The gate sensitive film for the sensor sensitive portion 31 is formed by potting a necessary original solution and drying the same for about more than 1 day in a drying chamber such as drying nitrogen atmosphere to splash the solvent.

In the manner described above, since the FETs 28 are formed on one surface of the sensor chip 25 and the sensor sensitive portions 31 are also formed on the other surface thereof, it becomes not necessary to positively carry out an insulation protection to the side of the sample flow passage 27 of the sensor chip 25 from the sample solution S. Accordingly, the surface, on the side of the sensor sensitive portions, of the sensor chip 25 and the wall surface of the sample flow passage 27 can be formed to be flat, thus being capable of making compact the outer shape of the flow cell sensor 22 and being effective for the trace quantity use of the sample solution S. Further, according to the structure of the present embodiment, an ISFET can be composed in which the gate sensitive portions 31 detecting ions through direct contact to the sample and output electrodes (FETs 28) such as drain source which is likely contaminated by ions or the like are separately formed on both the surfaces of the sensor chip 25.

Each of the FETs 28 of the sensor chip 25 is facedown connected to a polyimide flexible wire substrate 33, and according to this connection, the wirings from the respective FETs 28 can be led externally.

It is preferred for a smooth leading arrangement of the wiring from the sensor chip 25 that the output electrode on the side of the sensor chip 25 has a three-layer structure composed of gold/copper/titanium layers or a four-layer structure composed of gold/nickel copper/titanium layers, and the output electrode on the side of the flexible wiring substrate 33 is formed by a cream soldering coat treatment. In such treatment, it will be necessary that, in order to make small the outer diameter of the nozzle-type flow cell sensor 22, the flexible wiring substrate 33 is connected to the sensor chip 25 in an overlapped manner and that, in order to obtain a good connection condition, the surface of the soldered coat layer of the electrode is positioned higher than the surface of the cover coat layer insulating the surface of the flexible wiring substrate 33 other than the portion of the connected electrode. The flexible wiring substrate 33 may be formed so as to have a multi-layer structure so as to make compact the layout of the wiring line formed to the flexible wiring substrate 33. The flexible wiring substrate 33 and the sensor chip 25 thus formed are mated in their positions and then soldered and integrated through pulse heat treatment.

A water-resistant insulation layer 34 is formed on the surface of the nozzle-type flow cell sensor 22 except for the front nozzle portion 21a by coating a thermosetting resin such as epoxy resin. After the water-resistant insulation treatment, a coating such as of ethylene fluoride is effected to impart hydrophobic property to the surface of the flow cell sensor 22. The contamination of the outer surface of the flow cell sensor 22 can be reduced and the quantity of the sample to be treated with can be also reduced by effecting this coating treatment.

According to the nozzle-type flow cell sensor 22 of the present embodiment, the inner volume of the flow cell sensor 22 between the nozzle front end of the nozzle portion 21a and the sensor sensitive portion 31 can be remarkably reduced by about 2 μl in the case of the flow passage width being 1.00 mm and the length of the nozzle portion 22a of the sensor chip 25 being 5 mm.

The flow cell sensor utilized for the nozzle-type analysis apparatus of the present invention will be manufactured in the following manner.

A silicon substrate is first prepared, and the is silicon on one (first) surface of the silicon substrate subjected to the patterning treatment in shape of a stripe to thereby form the field electric transistors (FETs) 28. The openings 30 are then formed by, for example, aeolotropic etching treatment, to the other surface (second) of the silicon substrate at portions corresponding to the FETs 28 formed on the first surface thereof.

A film such as an insulation film of silicon oxide or gate passivation film of silicon nitride is then formed on the rear surface of the FET 28 exposed to the opening 30, thus forming the gate sensitive portion 31 and completing the sensor chip 25.

Thereafter, the thus completed sensor chip 25 is diced and then mounted in a state that the four FETs 28 for the temperature monitoring are arranged in a row of the numbers corresponding to the numbers of the necessary detection components, in the present embodiment, three ion components of sodium, potassium and chlorine ions.

Then, the polyimide flexible wiring substrate 33 is mated in position with this sensor chip 25 and integrated through the facedown connection through the pulse heat treatment, thus performing the wire draw-out from the FET 28 of the sensor chip 25.

After the sensor chip 25 and the flexible wiring substrate 33 have been integrated, the objective ion sensitive films are formed to the corresponding recessed portions of the gate sensitive portions 31 of the sensor chip 25. As occasion demands, films formed only of the base matrix materials are formed to the recessed portions of the temperature monitoring FETs so as to monitor the actual temperature of the sensor surface in conditions similar to those in the case of the formation of the ion sensitive films.

After the formation of the films to the recessed portions for the gate sensitive portions 31 of the sensor chip 25 and the temperature measurement recessed portions, the sensor chip 25 is bonded to the flow cell body 24, to which the flow passage grooves are preliminarily formed, by an organic bonding agent or electrostatic bonding means. For example, in the electrostatic bonding means, an electrode conducting to the silicon on the surface of the side reverse to the surface of the electrode side of the sensor chip 25 is formed and a high lead glass having a low melting point is preliminarily spattered to edges of the flow passage grooves.

Under the spatter formed state and after the sensor sensitive film formation, the sensor chip 25 and the flow cell body 24 are overlapped with each other in the mated state and voltage is then applied to them with a temperature ranging from a room temperature to about 60° to bond them. According to this operation, the sensor chip 25 and the flow cell body 24 can be electrostatically bonded without degrading the organic sensitive film (gate sensitive film) which is extremely weaken against the heating.

After the bonding and integrating the sensor chip 25 to the flow cell body 24, the thermosetting insulation resin such as epoxy resin is coated entirely on the outer periphery of the senser chip 25 and the flow cell body 24 including their connected portions, thus forming the water-resistant insulation layer 34 to achieve the water-resistant insulation protection. In order to impart the hydrophobic property to the surface of the flow cell sensor 22, a coat of a material such as ethylene fluoride is effected to the surface. According to this coating treatment, contamination on the outer surface of the nozzle cell can be significantly reduced.

According to the manner described above, the flow cell sensor 22, provided for the nozzle-type analysis apparatus, can be prepared. The prepared flow cell sensor 22 has the front end nozzle portion 21a integral with extended portions of the flow cell body 24 and the sensor chip 25, thus making the length of the nozzle portion 21a short. Further, in the described embodiment, the nozzle portion 21a is formed integrally and is dipped in the sample solution S, but in an alternation, to the flow cell sensor 22, an extended portion except for the sensor portion such as the gate sensitive portion 31 may be shortened or eliminated so that the sensor forming portion is directly dipped into the sample solution. Furthermore, the nozzle portion may be formed by separately bonding another nozzle chip made of such as stainless metal or Teflon, Trade Name, to the front end portion of the flow passage.

Figure 3:
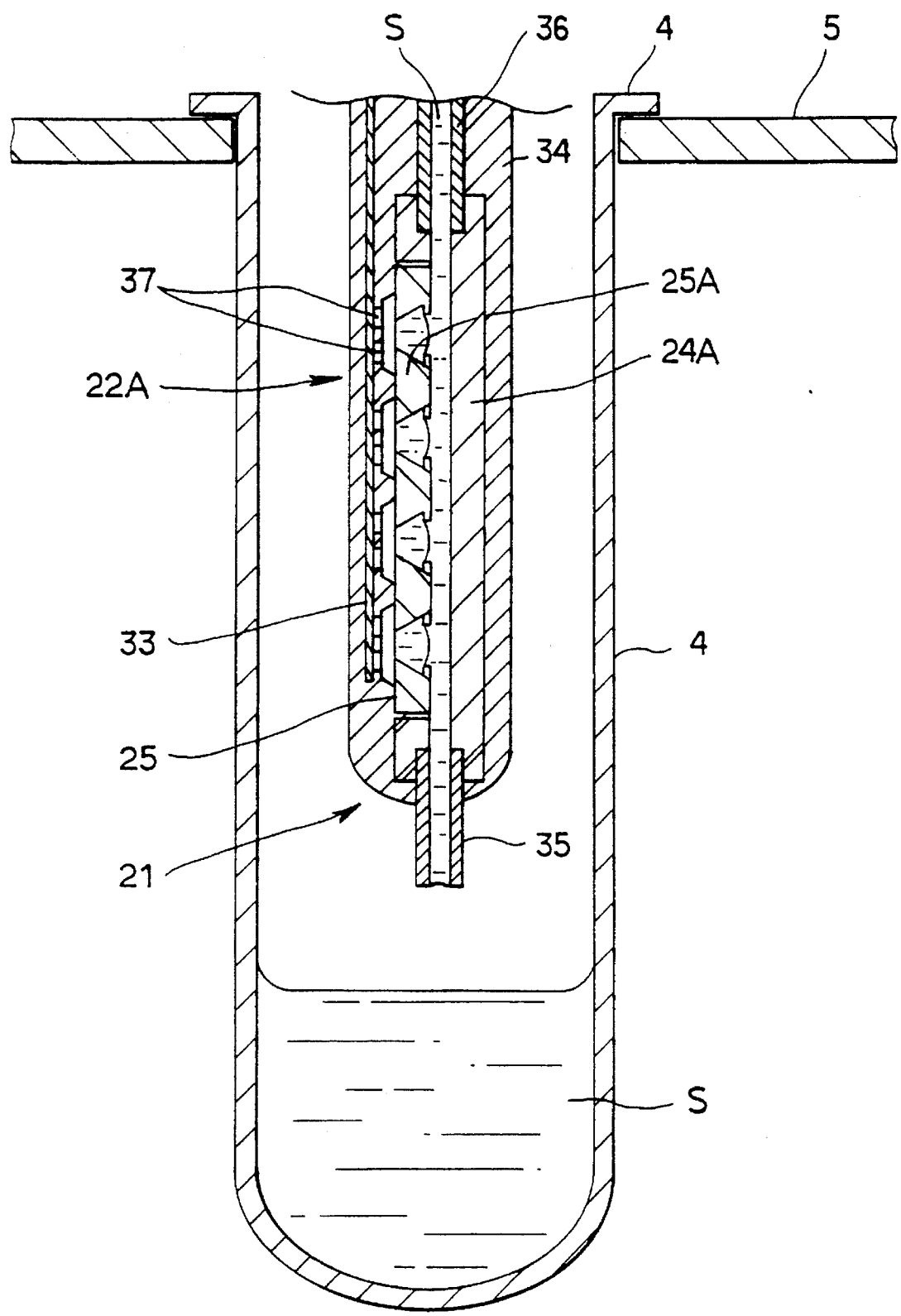
FIG. 3 is an elevational section of a second embodiment of the present invention.
Figure 4:
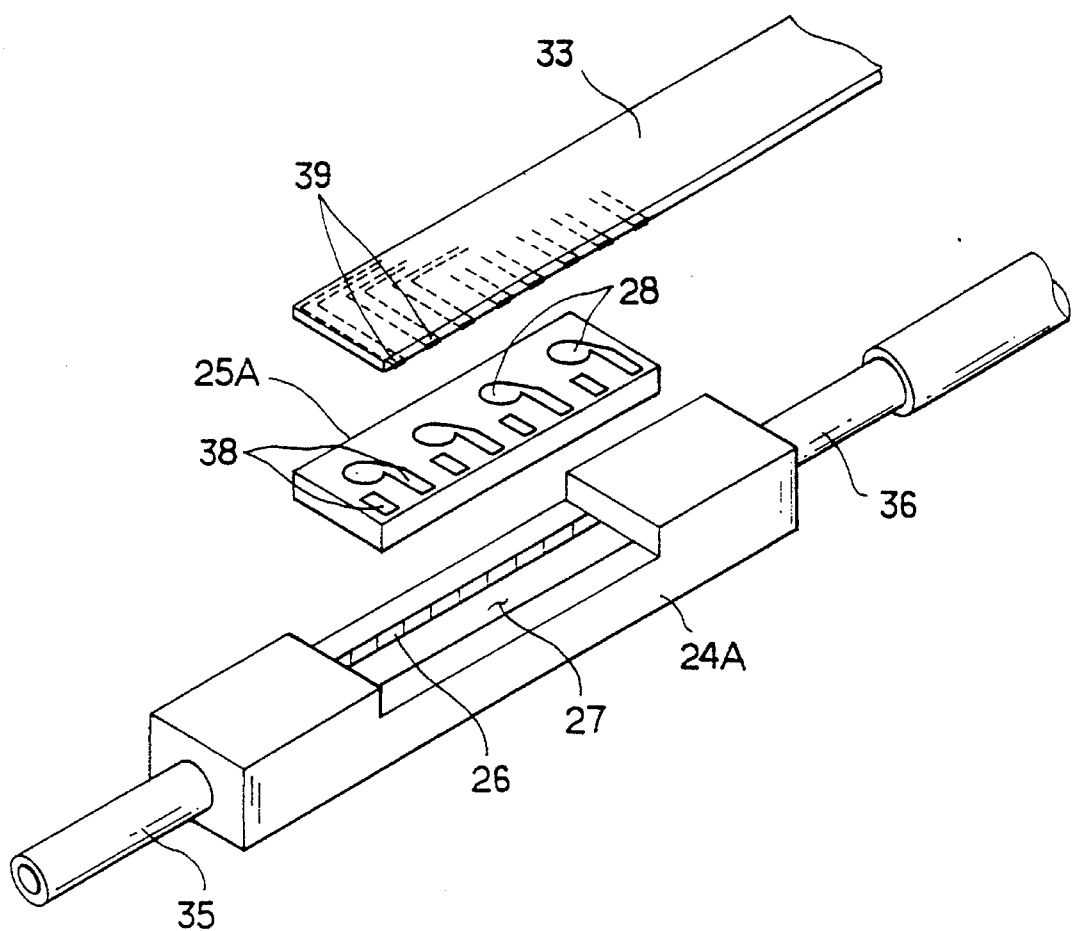
FIG. 4 is a developed perspective view of the solution component sensor of FIG. 3.

FIGS. 3 and 4 represent a second embodiment of the nozzle-type flow cell sensor 22A according to the present invention.

The flow cell sensor 22A of this embodiment is formed to the front end portion of the sample suction nozzle 21, in which a nozzle chip 35 and a sample suction tube 36 are preliminarily integrally connected to a flow cell body 24A constituting a cover, thus the nozzle portion being composed of the nozzle chip 35. According to this structure, since the nozzle chip 35 is preliminarily integrally connected to the flow cell body 24A, there is no need for forming any extension to the sensor chip 35.

The other structures of this embodiment shown in FIGS. 3 and 4 are substantially the same as those of the embodiment of FIGS. 1 and 2, so that like reference numerals are added to elements or portions corresponding to those of the former embodiment. Further, in FIGS. 3 and 4, a sensor output electrode 38 may be formed to the sensor chip 35, and an output electrode 39 formed to the flexible wiring substrate 33 is connected to the output electrode 38 in contact thereto.

According to the structure of the nozzle-type flow cell sensor 22A of the embodiment shown in FIGS. 3 and 4, the dimension of the sensor chip 35 can be minimized, and in addition, since it is not necessary to form a specific pattern of the nozzle chip to the chip surface, an array of the sensor can be formed in a solid form and the dicing operation can be flexibly done in accordance with the numbers of elements.

In an experiment regarding this embodiment, in which the nozzle-chip 35 was formed from a pipe having an inner diameter of 0.8 mm and a axial length of 5 mm, a dead volume of about 3 µl was observed, and a volume for the sensor portion was about 3 µl in the case of four element numbers, 1.0 mm flow passage width and 0.5 mm depth in this embodiment. Further, a Teflon tube was used for the nozzle chip 35, but a stainless tube may be also used therefor, and otherwise, the present invention may be operated without disposing the nozzle chip.

A measurement utilizing the nozzle-type flow cell censor 22A shown in FIGS. 3 and 4 was carried out approximately in the following manner.

A sample vessel having an inner dimension of 4 mm×5 mm and a depth of 40 mm was prepared, and a blood serum sample of the quantity of 5 µl was sampled in this material vessel. A tris-phosphate buffer solution was then added to the blood serum material to dilute the same 20 times.

Figure 5:
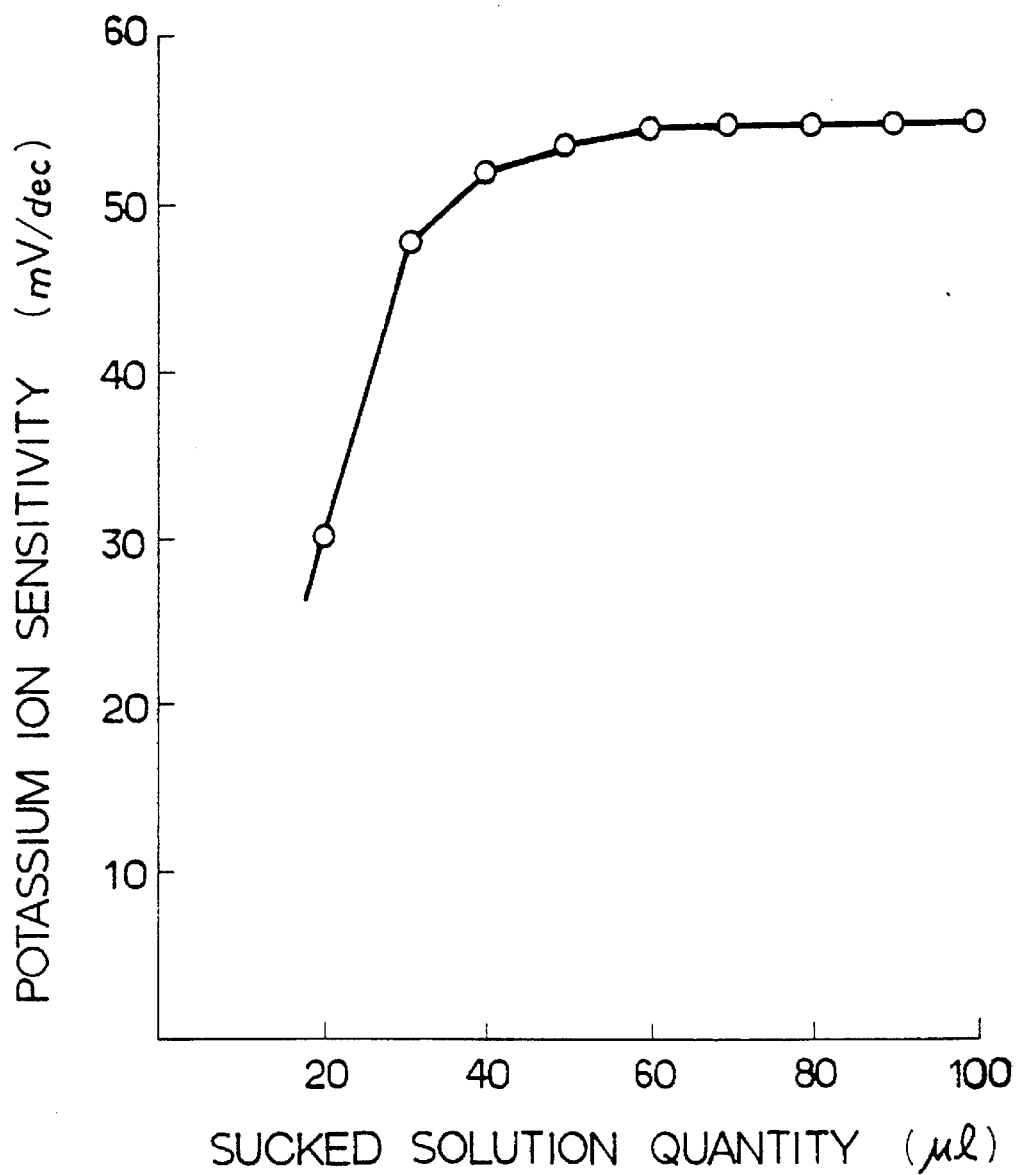
FIG. 5 is a graph showing relationship between a suction amount of a sample solution and a sensitivity of a potassium ion of a potassium sensor.

Thereafter, the nozzle-type flow cell sensor 22A was inserted into the sample vessel 4 and the sample solution S diluted by a displacement pump. The nozzle chip 35 was then lifted upward to position the front end thereof above the liquid surface of the diluted sample solution S remaining in the sample vessel 4, and an output was then detected and recorded. The quantity of the sample solution to be sucked was changed from 20 µl to 10 µl and the relationship between the sensitivity of the potassium ion sensor and the sucked quantity of the sample solution was examined. The result of this examination is represented by FIG. 5. As shown in FIG. 5, a saturated sensitivity was observed at the suction quantity of 60 µl, which showed that the quantity of the sample solution S necessary for the flow cell sensor of the present embodiment is very minute quantity of 3 µl.

In the result of the experiment of the relationship between the sensor temperature and the sensor cell position, it was found that the temperature was kept constant when the sensor cell portion was in the sample vessel 4, but the temperature was rapidly lowered when the sensor cell was taken out of the sample vessel 4. Further, the measurement is not limited in the sample vessel 4 of the sucked sample, but it may be done in another sample vessel disposed, on the same disc on which the sucked sample vessel 4 is disposed and the sensor cell of the flow cell sensor 22A may be otherwise measured at an area outside the sample disc at which the temperature is kept constant. For example, the flow cell sensor 22A as the sample suction nozzle is moved to a washing solution pool kept to the constant temperature by utilizing a mechanism for keeping the constant temperature of the sample disc 5 and the measurement will be then carried out at that washing solution pool. After the measurement, a washing treatment will be done.

In order to make more slow the stabilization of the temperature after the insertion of the nozzle-type flow cell sensor 22A into the sample vessel 4, it will be effective to make the temperature of the flow cell sensor 22A to a temperature near the sample temperature before the insertion into the sample vessel 4. In such case, it may be preferable to preliminarily keep the temperature of the flow cell sensor 22A to a temperature slightly higher than that of the sample vessel 4 in consideration of the temperature lowering during the movement of the flow cell sensor 22A. In an actual operation, a waiting space for heat reservation is provided above the reaction disc 5, or a waiting space for heat reservation utilizing a constant temperature keeping mechanism of the reaction disc 5 is provided at a portion near the reaction disc 5.

Figure 6:
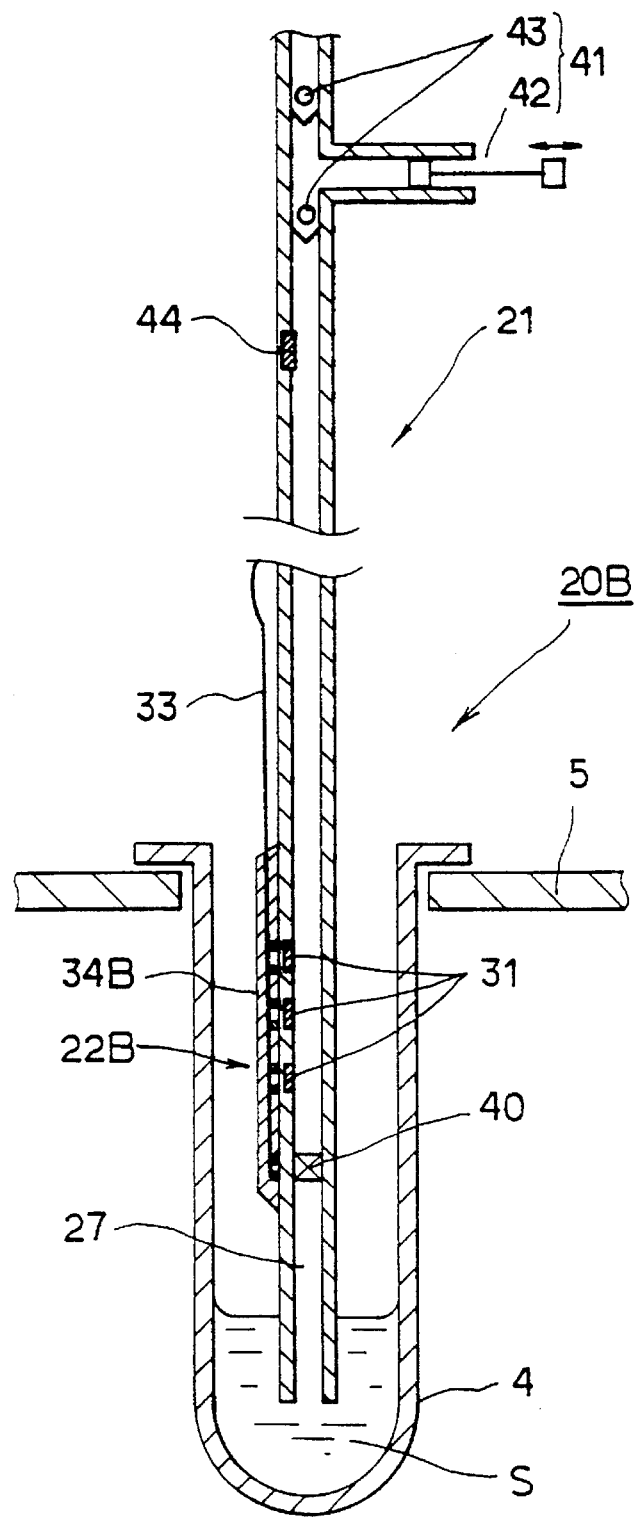
FIG. 6 is an elevational section of a third embodiment of the nozzle-type analysis apparatus of the present invention.

FIG. 6 represents a third embodiment of a nozzle-type analysis apparatus 20B, according to the present invention, provided with a flow passage shut-out valve.

In the nozzle-type analysis apparatus 20B, a flow cell sensor 22B constituting a solution component sensor is formed integrally or integrated with a portion of a sample suction nozzle 21 disposed to be inserted in or drawn out from the sample vessel 4 and a water-resistant insulation layer 34B is formed to at least a sensor output portion of the flow cell sensor 22B to impart the water-resistant property.

A solution flow shut-out valve 40 is disposed in the sample flow passage 27 at a portion between the front end of the sample suction nozzle 21 and the sensor sensitive portion 31 constituting the sensor forming portion of the flow cell sensor 22B. The solution flow shut-out valve 40 will be selected from a piezoelectric type one, an electrostatic type one, an air driving type one or an electromagnetic driving type one. Further, it is to be noted that like reference numerals are added in FIG. 6 to elements or portions of the nozzle-type analysis apparatus 20B corresponding to those of the nozzle-type analysis apparatus 20 of FIG. 1.

In the embodiment of FIG. 6, cross sectional areas of wiring arrangement of the flexible wiring substrate 33 and the sensor forming portion 31 of the flow cell sensor 22B including the sample passage are made smaller than an opening area of the sample vessel 4 to thereby make it possible to access the wiring arrangement and the sensor forming portion 31 in the sample vessel 4. Thus, according to this ebodiment, the length between the nozzle front end portion of the sample suction nozzle 21 and the sensor sensitive portion 31 is made short to reduce the dead space volume of the nozzle, thus remakably reducing the quantity of sample solution to be needed for the measurement.

Furthermore, as described above, since the solution flow shut-out valve 40 is disposed between the nozzle front end of the sample suction nozzle 21 and the sensor forming portion 31 in the sample flow passage 27, the flow condition of the sample solution S in the sample flow passage 27 can be regulated by the solution flow shut-out valve 40.

In practical, when it is required to measure the sample solution S as a material to be analyzed in the nozzle-type analysis apparatus, a sample suction pump 41 is driven to suck the sample solution S into the sample suction nozzle 21, and after the suction of the quantity of the sample solution S necessary for the operation of the sample suction pump 41, the solution flow shut-out valve 40 is closed to thereby make fast the flow of the sample solution S near the sensor sensitive portion 31 of the flow cell sensor 22B. The closing of the shut-out valve 40 makes it possible to increase a conduction resistance of the sample solution S in the sample vessel 4 to the sample solution near the sensor sensitive portion 31, thereby reducing the noise level. The solution flow shut-out valve 40 is also closed at a sample suction nozzle lifting time or moving time to prevent solution dropping or air bubbles.

The sample suction pump 41 is composed in combination of a piston cylinder assembly 42 and a check valve 43, and in this combination, the pump 41 is formed as a whole as a displacement pump. After the suction of the sample solution by pulling the piston cylinder assembly 42, a positive pressure is applied to the sensor area by quickly applying a pressure by moving the piston cylinder assembly in the direction reverse to the pulling direction as arrowed in FIG. 6, whereby the trailing of the sample flow can be suppressed. Such pressure applying operation can be easily done by means of the displacement pump and no new means is required for the purpose for this analysis apparatus. Furthermore, since in this apparatus, no driving force is required for the check valve 43, the analysis apparatus can be itself made compact, thus being advantageous. In this embodiment, a reference electrode 44 is provided to the sample suction nozzle 21. The reference electrode 44 is shown in FIG. 6 as being disposed on an inner wall of the suction nozzle 21 and shows the reference electrode is separated from the front end portion of the sample suction nozzle 21.

FIG. 7 represents a modified embodiment of a nozzle-type analysis apparatus 20C in which a check valve 45 is provided in place of the solution flow shut-out valve 40 in the embodiment of FIG. 6. The structure of the nozzle-type analysis apparatus 20C of FIG. 6 has substantially the same structure, other than this check valve 45, as that of FIG. 7, so that like reference numeral are added to elements or portions corresponding to those of FIG. 6 and the detailed explanation thereof is omitted herein for the sake of convenience.

Figure 8:
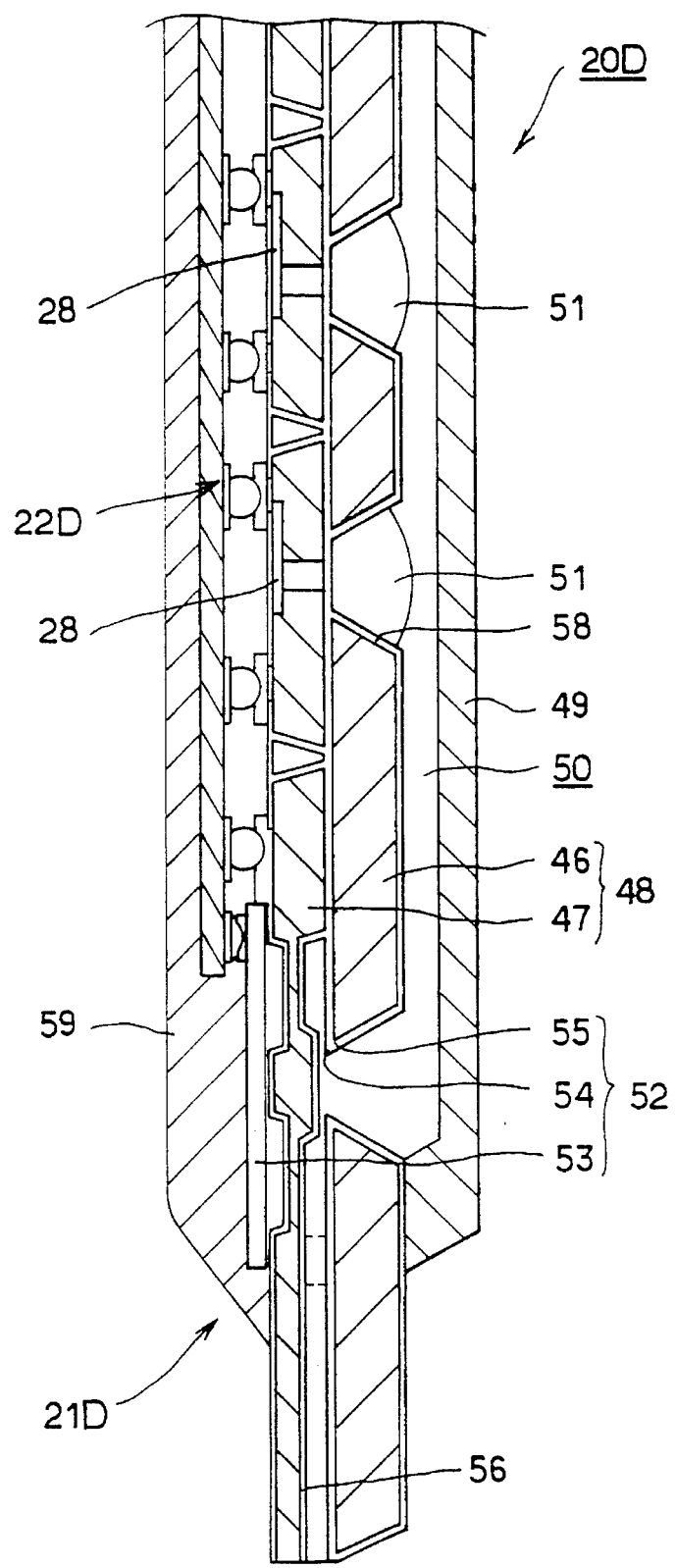
FIG. 8 is also an elevational section of a further embodiment of the nozzle-type analysis apparatus of the present invention.

FIG. 8 represents a further embodiment of a nozzle-type analysis apparatus 20D of a valve integrated type according to the present invention.

This nozzle-type analysis apparatus 20D is composed of a flow cell sensor 22D as a solution component sensor provided with a rear gate-type ion sensitive field effect transistor ISFET 28, and the flow cell sensor 22D is formed at the front end portion of a sample suction nozzle 21D.

In this flow cell sensor 22D, a sensor chip 48 is formed by securing a sensor plate 47 to one side of a plate-like flow cell body 46 constituting a base silicon substrate and a cover member 49 is secured to the other side of the flow cell body 46, whereby a sample flow passage 50 is formed inside the sample suction nozzle 21D. The sample flow passage 50 has a sample intake portion formed to an extension of the flow cell body 46 and the sensor plate 47 and has a flow passage on the side of the sensor sensitive portion 51 formed between the flow cell body 46 and the cover member 49. A solution flow shut-out valve 52 is disposed at a flow changing portion of the sample flow passage 50 and this solution flow shut-out valve 52 is a piezoelectric type microvalve comprising a piezoelectric element 53, a valve diaphragm 54 and a valve sheet 55. According to the operation of the piezoelectric element 53, the valve diaphragm 54 is displaceable on the side of the valve sheet 55, whereby the sample passage 50 can be temporarily closed.

The ISFET 28, the piezoelectric type microvalve 52 and a flow passage groove 56 for forming the nozzle front end portion are integrally formed to the sensor plate 47 formed as a silicon wafer. The sensor chip 48 is formed by bonding, to the flow cell body 46, the sensor plate 47 to which the flow passage groove 56 and the valve diaphragm 54 are worked through oxide film.

After the bonding of the flow cell body 46 to the sensor plate 47, the silicon on the first surface of the sensor chip 52 is patterned in a shape of stripe, and spaces between element islands are embedded with $SiO_2$ and poly-Si layers to thereby carry out dispersion of impurities for the FET and shaping working to the front surface side of the valve diaphragm 54.

In the next step, the openings 58 are formed through, for example, aeolotropic etching treatment to the second surface of the flow cell body 46 at portions corresponding to the locations of the FETs 28 and the valve diaphragms 54, and the sensor sensitive portions 51 are also formed by forming the oxide silicon gate insulation films or gate passivation films of, for example, silicon nitride on the rear surface of the FETs 28 exposed to the bottoms of the openings 58. The positive conductive plate 53 is bonded to the valve diaphragm 54 of the microvalve 52. According to such structure, the gate sensitive portions 51 directly contacting the sample solution S and detecting ions or the like is formed on one surface of the sensor chip 48 and the output electrodes 28 and the valve driving portion 53 weak against the contamination of ions are formed, separately from the gate sensitive portions 51, on the other surface of the sensor chip 48.

The thus completed sensor chip 48 were diced with respect to the respective FETs 28 of the numbers corresponding to the necessary detection components and then mounted in the system. In the present embodiment, two FETs, corresponding to the two ion component elements of sodium and potassium, and the microvalve are arranged in a row as one chip.

The wiring arrangement from this sensor chip 48 is performed through the facedown connection between the sensor chip 48 and the polyimide flexible wiring substrate 33. For this purpose, the output electrode on the side of the sensor chip 48 has the three-layer structure of gold/copper/titanium or four-layer structure of gold/ nickel/copper/titanium, and the electrode on the side of the flexible wiring substrate 33 was subjected to cream soldering coating treatement. In this operation, the flexible wiring substrate 33 was disposed in an overlapped manner on the sensor chip 48 to make small the outer shape of the nozzle-type flow cell sensor 22D of this embodiment.

The thus prepared flexible wiring substrate 33 was mated in positions with the sensor chip 48 and then heated through the pulse heat treatment to thereby effect the soldering.

Next, the sensitive films of the ions were formed to the corresponding sensor sensitive portions 51 as the sensor body of the flow cell sensor 22D. Preferably, the potassium ion film is composed of, for example, valinomycin utilized as a sensing material and polyvinyl chloride utilized as a matrix material. The sodium ion film is composed of, for example, biscrown ether utilized as a sensing material and polyvinyl chloride as a matrix material. These sensing materials and the matrix materials were mixed with a plasticizer and a solvent and then potted to the openings 58 by means of a microdispenser. In this operation, when cyclohexanon is utilized as the solvent, the potting can be done smoothly without rapidly drying the trace quantity of original liquid. After the potting of the necessary quantity of the original solution, the sensitive film materials were dried for about more than one day in a drying chamber, thus obtaining the product films.

The cover members 49 were then bonded to the sensor chips 47. The flow passage groove had already been formed to the cover member 49 by forming the flow groove such as V-shaped groove to the silicon substrate through isotropic etching treatment. The electrostatic bonding means or organic bonding agent may be optionally utilized for the bonding treatment.

In the next step, the water-resistant insulation layer 59 formed of an epoxy resin having water-resistant insulation property was coated on the sensor output portion constituting the connection portion between the sensor chip 47 and the flexible wiring substrate 33 or entirely thereon to achieve the water-resistant insulation protection. In order to make the surface thereof hydrophobic, the coating of such as ethylene fluoride coating was effected. This coating was effective for reducing the possibility of the contamination on the outer surface of the nozzle cell.

Although two sensor sensitive portions 51 are formed in the embodiment of FIG. 8, more than two sensor sensitive portions may be formed, and in the case of plural sensor sensitive portions 51, the sensitive portions 51 may be arranged in plural rows, or the sensor chips 48 are provided in place of the cover member 49 and the sample passage 50 may be formed between the sensor chips 48.

The measurement in the use of the nozzle-type flow cell sensor 22D of the structure described above will be carried out approximately in the following manner.

In an experiment in the present embodiment, in which the sample vessel 4 having inner dimension of 4 mm×5 mm and depth of 40 mm was used and the blood serum sample of 5 µl was added in this sample vessel 4 to prepare the sample solution S. A tris-phosphate buffer solution was then added to the sample solution S to dilute the same 20 times.

Thereafter, the nozzle-type flow cell sensor 22D was inserted into the sample vessel 4 and the sample solution S diluted by a displacement pump. At an instance of the completion of the pump sucking operation (about one minute), DC voltage of 100 V was applied between the microvalve electrodes to thereby flex the piezoelectric element 53, thus closing the microvalve 52.

Figure 9:
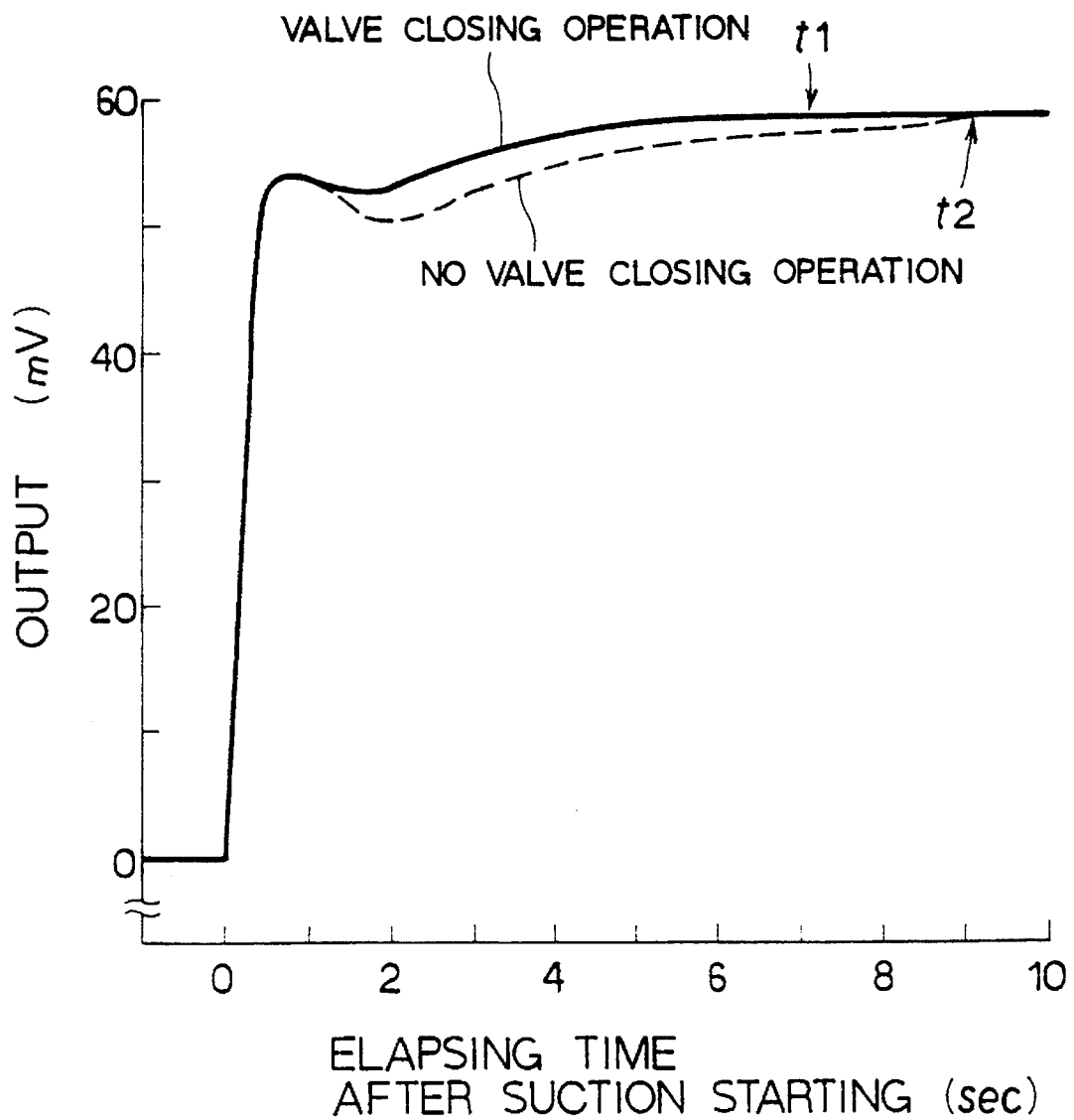
FIG. 9 is a graph representing a response characteristics of the operation of a sample flow shut-out valve provided for the nozzle-type analysis apparatus of FIG. 8.

FIG. 9 shows a graph representing a response characteristics in the case of the microvalve 52 being opened or closed. In the case where the microvalve 52 does not include the closing operation, the time t2 reaching the stable condition was about 9 secds., whereas in the case where the microvalve 52 is in the closing operation, the time t1 reaching the stable condition was about 7 secds, which results in that the stable condition can be achieved further smoothly through the use of the microvalve 52. Furthermore, in the case of no microvalve 52, it was necessary to dip the front end of the nozzle into the sample solution for about 3 secds, in maximum, after the sucking operation, for preventing the air involving into the sample suction nozzle 21D. On the contrary, in the case of the use of the microvalve 52, the nozzle can be lifted up immediately after the closing of the microvalve 52 after the suction of the sample solution S, thus being advantageous.

What is claimed is:

1. An analysis apparatus for sucking a sample solution in a sample vessel for analyzing the sample solution comprising:

a sample suction nozzle means having defined therein a channel through which a sample is suctioned;

an elongated front end portion attached to the sample suction nozzle means for sucking the sample solution stored in the sample vessel;

a solution component sensor means having a sensor forming portion formed integrally with an inner portion of the sample suction nozzle means to be inserted into the sample vessel, said solution component sensor means including an output portion for outputting signals, the integral structure of said sample suction nozzle means and said solution component sensor means having a size which fits into a sample vessel along with the elongated front end portion;

a water-resistant insulation layer formed outside said solution component sensor means for substantially covering the sensor forming portion including the output portion; and a reference electrode means disposed inside the sample suction nozzle means in communication with said channel at a portion downstream from the solution component sensor means with respect to the flow of the sample in a sample sucking direction.

2. An analysis apparatus according to claim 1, wherein said solution component sensor means comprises a flow cell sensor which comprises a flow cell body, a plate-shaped sensor chip bonded to the inside of said flow cell body and a sample flow passage formed in an axial direction of the flow cell body.

3. An apparatus according to claim 2, wherein said sensor chip is integrally bonded to said flow cell body through an electrostatic bonding means.

4. An analysis apparatus according to claim 2, wherein said flow cell body includes a silicon substrate and said sample flow passage is composed of a V-shaped groove section formed by effecting an isotropic etching treatment to said silicon substrate.

5. An analysis apparatus according to claim 2, wherein said flow cell body is formed of a glass material.

6. An analysis apparatus according to claim 2, wherein said flow cell body is formed of an acrylic resin.

7. An analysis apparatus according to claim 2, wherein said flow cell body has an exterior surface coated with a hydrophobic film to eliminate surface contamination.

8. An analysis apparatus according to claim 2, wherein said sensor chip is composed of a silicon substrate having a multi-layer structure.

9. An analysis apparatus according to claim 8, wherein said sensor chip is composed of a silicon substrate having a three-layer structure of silicon/oxide-film/silicon layers.

10. An analysis apparatus according to claim 9, wherein said silicon substrate has one layer to which a plurality of field effect transistors are formed in a row.

11. An analysis apparatus according to claim 10, wherein said silicon substrate has another layer to which a plurality of openings are formed at portions corresponding to the location of said field effect transistors and gate insulation films or gate passivation films are formed on surfaces of the field effect transistors on the sides exposed to the openings to thereby form sensor sensitive portions.

12. An analysis apparatus according to claim 2, wherein said water-resistant insulation layer further coats said flow cell sensor and is formed by coating a thermosetting resin on the surface of the flow cell sensor end.

13. An analysis apparatus according to claim 1, further comprising a sample flow shut-off valve means disposed in said channel at a portion between the elevated front end portion of the sample suction nozzle means and the sensor forming portion of the solution component sensor means.

14. An analysis apparatus according to claim 13, wherein said sample flow shut-off valve means comprises a check valve.

15. An analysis apparatus according to claim 13, wherein said sample flow shut-off valve means is integrally formed to said solution component sensor means.

16. An analysis apparatus according to claim 15, wherein said sample flow shut-off valve means is a microvalve which comprises: a piezoelectric element laminated to a valve sheet and a valve diaphragm, which is displaceable towards the valve sheet, wherein the diaphragm is flexed by the piezoelectric element such that the valve sheet engages the diaphragm, shutting off sample flow to the solution component sensor means.

17. An analysis apparatus according to claim 16, wherein said solution component sensor means comprises a flow cell sensor which comprises a flow cell body, a sensor chip bonded to an inside of said flow cell body and a sample flow passage formed in an axial direction of the flow cell body, and wherein said microvalve is disposed in the sample flow passage.

18. An analysis apparatus according to claim 17, wherein said flow cell sensor comprises a flow cell body as a base silicon substrate, a sensor plate forming a sensor chip formed on one side of the flow cell body and a cover member disposed opposite the sensor chip, said sample flow passage being formed between the sensor chip and the cover member.

19. An analysis apparatus according to claim 2, wherein said flow cell sensor comprises an ion sensitive field effect transistor.

20. An analysis apparatus according to claim 1, further comprising:
a water-resistant insulation layer covering the entire sensor output portion of said solution component sensor means.

21. An analysis apparatus for analyzing a sample solution in a sample vessel comprising:
a sample suction nozzle forming an internal channel through which a sample solution is suctioned, and including a front nozzle portion for dipping into a sample solution during an analysis;
a sensor means having a sensitive portion integrally formed along the internal channel and in communication with the sample solution during the analysis and extending to an exterior of the sample suction nozzle for connection to wiring;
wherein, the sensitive portion provides a seal to prevent contamination of the internal channel;
wherein, the front nozzle portion is elongated to prevent contamination of the sensor means; and
wherein, a portion of the analysis apparatus, including the front nozzle portion, the sensor means in the sample suction nozzle and the wiring, fits within a sample vessel during the analysis.

22. The apparatus of claim 21, wherein the portion of the analysis apparatus, including the front nozzle portion, the sensor means in the sample suction nozzle and the wiring, fits within a sample vessel which has a cross-sectional width as small as 4 mm, a cross-sectional length as small as 5 mm and a depth as small as 40 mm.

23. The apparatus of claim 22, wherein the analysis apparatus can successfully analyze a sample solution having an amount as small as 5 μl.

24. The apparatus of claim 23, wherein the front nozzle portion has a length of 5 mm.

25. The apparatus of claim 24, wherein the internal channel has a diameter of 1 mm.

26. The apparatus according to claim 22, wherein the sensor means further comprises:
a plurality of sensors each having a sensitive portion integrally formed along the internal channel and in communication with a sample solution during the analysis and extending to an exterior of the sample suction nozzle for connection to wiring; and
a plurality of semiconductor transistors diced out of a semiconductor substrate and packaged in a single row to form a semiconductor sensor chip of compact size for allowing the sensor means in the sample suction nozzle to fit into a sample vessel,
wherein, the transistors of the semiconductor sensor chip are aligned on one side with the sensitive portions formed in the sample suction nozzle, a wiring substrate is formed in contact with the transistors on an opposite side to the sensitive portions, and an insulation layer covers the semiconductor sensor chip and the wiring substrate to protect the transistors and to prevent contamination of the internal channel.

27. The apparatus of claim 26, wherein the plurality of sensors further comprise:
a temperature sensor for sensing the temperature within a sample vessel during the analysis.

28. The apparatus of claim 26, further comprising:
a shut-off valve located within the internal channel and between the plurality of sensors and the front nozzle portion for closing the front nozzle portion;
wherein, the analysis may be completed with the front nozzle portion withdrawn from a sample solution when the shut-off valve is closed; and
wherein, the shut-off valve also fits within a sample vessel.

29. The apparatus of claim 28, further comprising:
a reference electrode having a sensitive portion in communication with the internal channel.

30. The apparatus of claim 22, wherein the sample suction nozzle further comprises:
a sensor plate forming one side of the sample suction nozzle, and having an opening therein for connecting a transistor to the sensitive portion, said transistor being located on an opposite side of the sensor plate to the internal channel;
a flow cell body disposed on said sensor plate and protruding into the internal channel for holding the sensitive portion in connection to the transistor; and
a cover member forming another side of the sample suction nozzle;
wherein, the front nozzle portion is defined by an internal channel through which a sample solution is suctioned between the sensor plate and the flow cell body; and
wherein, the flow cell body includes an opening after the front nozzle portion for redefining the internal channel as being between the flow cell body and the cover member.

31. The apparatus of claim 30, further comprising:
a shut-off valve employing a diaphragm which seals the opening in the flow cell body located after the front nozzle portion for shutting off the internal channel defined by the flow cell body and the cover plate.

* * * * *